United States Patent [19]

Okabe et al.

[11] 4,342,774
[45] Aug. 3, 1982

[54] N-ACYLCARNOSINE ALUMINUM SALT, ITS PREPARATION, AND A DIGESTIVE ULCER REMEDY CONTAINING SUCH SALT

[75] Inventors: Susumu Okabe, Kyoto; Takashi Sonehara, Mitaka; Masaru Sato, Koshigaya; Mitsuo Mazaki, Chiba, all of Japan

[73] Assignee: Nippon Chemiphar Co., Ltd., Tokyo, Japan

[21] Appl. No.: 185,774

[22] Filed: Sep. 10, 1980

[30] Foreign Application Priority Data

Sep. 13, 1979 [JP] Japan .................. 54-116717

[51] Int. Cl.³ .................. A61K 33/06; C07D 233/64
[52] U.S. Cl. .................. 424/273 R; 548/104
[58] Field of Search ............ 548/104; 424/255, 273 R

[56] References Cited

U.S. PATENT DOCUMENTS 3,746,700 8/1971 Erba .................. 548/104
4,233,310 11/1980 Fujita et al. .................. 424/273

FOREIGN PATENT DOCUMENTS 41-414384 8/1966 Japan .................. 424/255

*Primary Examiner*—Thomas A. Waltz
*Assistant Examiner*—Raymond Covington
*Attorney, Agent, or Firm*—Oblon, Fisher, Spivak, McClelland & Maier

[57] ABSTRACT

An N-acylcarnosine aluminum salt of the formula,

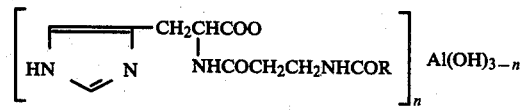

wherein R represents a lower alkyl group having 1 to 6 carbon atoms, a phenyl group or a lower alkoxy group-substituted phenyl group, and n is an integer of 1 to 3 is effective for use as a digestive ulcer-remedying or anti-ulcer agent.

15 Claims, No Drawings

N-ACYLCARNOSINE ALUMINUM SALT, ITS PREPARATION, AND A DIGESTIVE ULCER REMEDY CONTAINING SUCH SALT

BACKGROUND OF THE INVENTION

1. Field of the Invention

This invention relates to novel N-acylcarnosine compounds, and more particularly, to an N-acylcarnosine aluminum salt, its preparation, and a digestive ulcer remedy containing such salt.

2. Description of the Prior Art

In recent years, there has been a trend toward the increase of patients suffering from a digestive or peptic ulcer, and various attempts have been made to develop remedies for the ulcer.

The present inventors have synthesized a number of compounds and have investigated their pharmaceutical effects. As a result of this investigation, it has been found that N-acylcarnosine compounds of a specific type, which will appear hereinafter, exhibit a significantly excellent digestive ulcer-remedying or anti-ulcer effect and are low in toxicity and hence are satisfactory for actual use. Based upon this finding, the present invention has been accomplished.

SUMMARY OF THE INVENTION

Therefore, one object of the present invention is to provide a novel N-acylcarnosine aluminum salt.

Another object of the invention is to provide a novel process for preparing an N-acylcarnosine aluminum salt.

A further object of the invention is to provide a novel digestive ulcer remedy which comprises an effective amount of an N-acylcarnosine aluminum salt.

Briefly, these objects and other objects and advantages of this invention can be attained by an N-acylcarnosine aluminum salt of the formula (I),

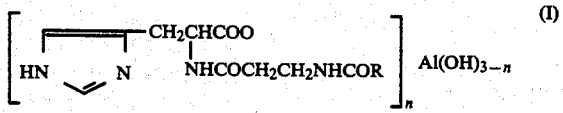

wherein R represents a lower alkyl group containing 1 to 6 carbon atoms, a phenyl group or a lower alkoxy group-substituted phenyl group, and $n$ is an integer of 1 to 3.

DETAILED DESCRIPTION OF THE INVENTION

The N-acylcarnosine aluminum salt of the formula (I) according to the present invention can be prepared, for example, by interacting an N-acylcarnosine of the formula (II),

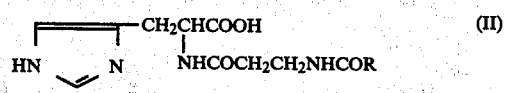

wherein R has the same meaning as defined above, which an aluminum alkoxide or an inorganic aluminum salt by any of the methods described below.

Method 1

An N-acylcarnosine is reacted with an aluminum alkoxide to obtain an N-acylcarnosine aluminum salt of the formula (I).

The acylcarnosine useful as one of the starting materials is prepared, for example, by converting the corresponding carboxylic acid to an acid halogenide in any usual manner and then reacting the halogenide with carnosine.

Typical examples of the aluminum alkoxide include aluminum methoxide, aluminum ethoxide, aluminum isopropoxide, aluminum t-butoxide, aluminum cyclohexyloxide and the like. When the aluminum alkoxide contains any impurity such as aluminum hydroxide or a polymer thereof, it is preferable to remove the impurity by distillation, solvent extraction or the like. The reaction is favorably conducted in a suitable solvent at a temperature ranging from room temperature to 80° C. Suitable solvents include water, an organic solvent such as methanol, ethanol, isopropanol or butanol, and a mixture thereof. After completion of the reaction, the solvent and secondarily produced alcohols are removed from the reaction solution to obtain the desired N-acylcarnosine aluminum salt of the formula (I).

Method 2

An N-acylcarnosine is reacted with an inorganic aluminum salt, and the resulting aqueous reaction solution is passed through a column packed with an anion exchange resin to obtain the desired N-acylcarnosine aluminum salt of the formula (I).

Typical examples of the inorganic aluminum salt useful in method 2 include mineral acid salts of aluminum such as aluminum sulfate, aluminum nitrate and aluminum chloride.

The anion exchange resin useful in method 2 may be either a weakly basic resin or a strongly basic resin, and preferably, a weakly basic anion exchange resin such as Amberlite IR-45 is used.

The amount of the anion exchange resin depends on the amount of the ions of a mineral acid and on the type of the ions in an aqueous solution of the N-acylcarnosine and the mineral acid. Too small amounts of such resin adversely cause the mineral acid ions to introduce into an effluent, while excessive amounts induce the adsorption of the N-acylcarnosine to an objectionable degree. Accordingly, it is desirable that the anion exchange resin be used twice or three times equivalent of the N-acylcarnosine.

The concentration of the aqueous solution which is passed through the column is not critical but is preferably held at such a level that the concentration of the mineral acid ions is in the range of about 0.5 to 1 equivalent per liter of the solution. The space velocity is suitably in the range of about 0.5 to 2.

The aqueous solution which has come out of the column is concentrated under reduced pressure and evaporated to dryness to obtain the desired compound of the formula (I).

In either method 1 or method 2 above, when the molar ratio of an N-acylcarnosine to an aluminum alkoxide or an inorganic aluminum salt is varied, an N-acylcarnosine aluminum salt can be prepared which corresponds to such molar ratio.

The N-acylcarnosine aluminum salts typical of and practical for the present invention which were listed as samples A or I were tested to determine their digestive ulcer-curing effects and degrees of toxicity with the results tabulated in the following experimental examples.

Samples:

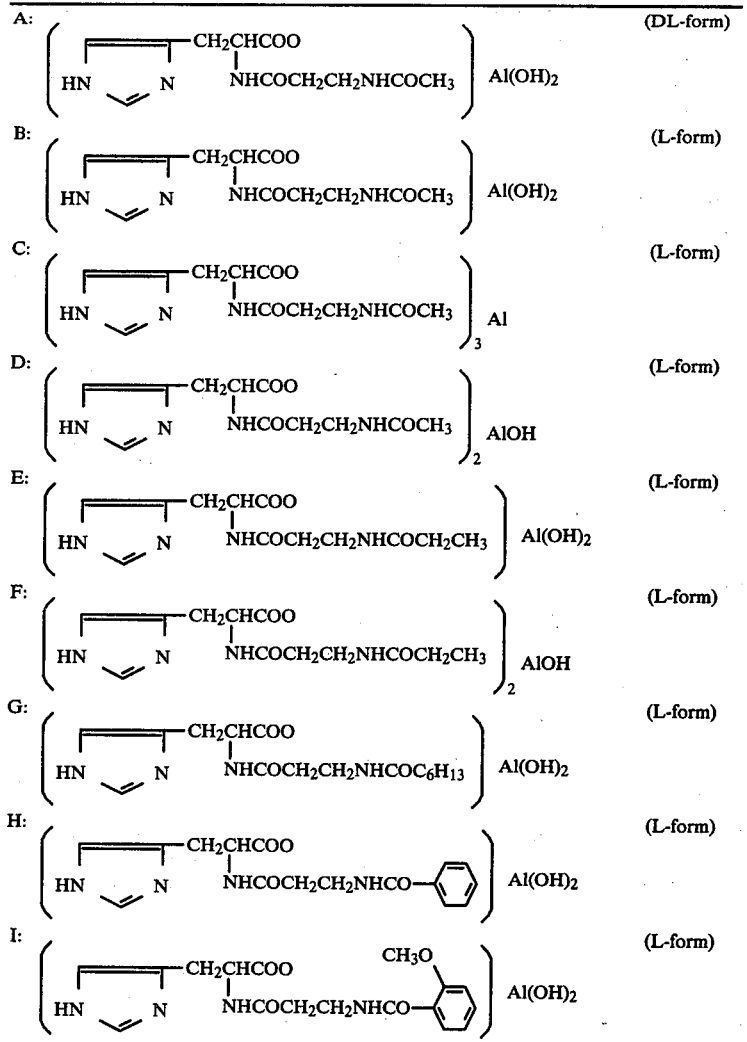

It will be noted that as control compounds for the purposes of comparison, use was made of L-carnosine, L-glutamine, N-acetyl-L-glutamine aluminum and aluminum sucrose sulfate which are known to have an anti-ulcer effect. The anti-ulcer effects and degrees of toxicity of the N-acylcarnosine aluminum compounds according to the invention were determined using rats in which instances various gastric ulcer models of rats were utilized to estimate the anti-ulcer effects.

The experimental methods of ulcers and toxicity will be apparent from the following description.

EXPERIMENT 1

Shay's ulcer: Groups of ten male Donryu strain rats each weighing 210 to 230 g were deprived of food for 48 hours. The pylorus of each rat was ligated according to the method of Shay et al [Gastroenterology, 5, 43–61 (1945)]. Each of the animals was allowed to stand abstained from food and water for further 14 hours and then sacrificed to remove its stomach. After collection of the gastric juice, the ulcerated area (mm$^2$) in the forestomach of each rat was measured under a dissecting microscope (10x). The total area (mm$^2$) of all the lesions of each rat was indicated as an ulcer index. Test medicine samples were given orally immediately after the pylorus ligation.

The experimental results are shown in Table 1.

TABLE 1

| Inhibitory Effects on Shay's Ulcer on Rats | | | |
|---|---|---|---|
| Samples | Dose (mg/kg, P.O.) | Ulcer index | % Inhibition |
| Control | — | 2.4 ± 0.7 | — |
| A | 1,000 | 0.5 ± 0.5 | 79.2 |
| L-Carnosine | 1,000 | 2.1 ± 0.7 | 12.5 |
| L-Glutamine | 1,000 | 2.2 ± 0.8 | 8.3 |
| Aluminum sucrose sulfate | 1,000 | 0.7 ± 0.8 | 71.7 |
| Control | — | 2.5 ± 0.7 | — |
| B | 1,000 | 0.6 ± 0.4 | 76.0 |
| L-Carnosine | 1,000 | 2.2 ± 0.8 | 12.0 |
| L-Glutamine | 1,000 | 2.3 ± 0.7 | 8.0 |
| N-Acetyl-L-glutamine aluminum | 2,000 | 0.7 ± 0.6 | 72.0 |
| Aluminum sucrose sulfate | 1,000 | 0.8 ± 0.9 | 68.0 |
| Control | — | 2.9 ± 0.4 | — |
| C | 1,000 | 1.0 ± 0.7 | 65.5 |
| D | 1,000 | 0.9 ± 0.9 | 69.0 |

TABLE 1-continued

Inhibitory Effects on Shay's Ulcer on Rats

| Samples | Dose (mg/kg, P.O.) | Ulcer index | % Inhibition |
|---|---|---|---|
| N-Acetyl-L-glutamine aluminum | 2,000 | 0.9 ± 0.7 | 69.0 |
| Aluminum sucrose sulfate | 1,000 | 0.8 ± 0.6 | 72.4 |
| Control | — | 3.1 ± 1.1 | — |
| E | 1,000 | 0.7 ± 0.5 | 77.4 |
| F | 1,000 | 0.9 ± 0.7 | 71.0 |
| G | 1,000 | 0.9 ± 1.0 | 71.0 |
| H | 1,000 | 1.0 ± 0.9 | 67.7 |
| I | 1,000 | 1.1 ± 0.8 | 64.5 |
| N-Acetyl-L glutamine aluminum | 2,000 | 1.0 ± 0.6 | 67.7 |
| Aluminum sucrose sulfate | 1,000 | 0.9 ± 0.5 | 71.0 |

EXPERIMENT 2

Stress ulcer: Groups of ten male Donryu strain rats each weighing 240 to 260 g were placed in a stress cage which served to immobilize the animals therein and then immersed in a water bath of 23° C. on a level with the xiphoid process according to the method of K. Takagi et al [Jap. J. Pharmac., 18 (9), 9–19 (1968)], thereby imposing stress on each rat. Seven hours after the immersion, each of the animals was withdrawn from the water bath and immediately sacrificed by a blow on the head, followed by removal of the stomach of each rat. The stomach was slightly inflated by injecting a 1% formalin solution and then immediately immersed in a 1% formalin solution, followed by incising the stomach along its greater curvature to measure the length (mm) of each lesion in the glandular portion under a dissecting microscope (10x). The total length (mm) of all the lesions of each rat was indicated as an ulcer index. Test medicine samples were given orally ten minutes before the immersion in water.

The results are shown in Table 2.

TABLE 2

Inhibitory Effects on Stress Ulcer in Rats

| Samples | Dose (mg/kg, P.O.) | Ulcer index | % Inhibition |
|---|---|---|---|
| Control | — | 15.2 ± 3.2 | — |
| A | 300 | 8.0 ± 2.8 | 47.4 |
|  | 1,000 | 4.4 ± 2.2 | 71.1 |
| L-Carnosine | 300 | 14.2 ± 3.7 | 6.6 |
|  | 1,000 | 10.7 ± 2.2 | 29.6 |
| Aluminum sucrose sulfate | 1,000 | 6.5 ± 6.0 | 56.7 |
| Control | — | 17.5 ± 3.5 | — |
| B | 300 | 9.2 ± 3.0 | 47.4 |
|  | 1,000 | 4.8 ± 2.6 | 72.6 |
| L-Carnosine | 300 | 16.0 ± 4.0 | 8.6 |
|  | 1,000 | 12.1 ± 2.5 | 30.9 |
| N-Acetyl-L-glutamine aluminum | 2,000 | 5.5 ± 4.8 | 68.6 |
| Aluminum sucrose sulfate | 1,000 | 7.3 ± 6.8 | 58.3 |

A and B have the same meaning as defined above.

EXPERIMENT 3

Aspirin-induced ulcer: Groups of ten male Donryu strain rats each weighing 220 to 230 g were deprived of food for 24 hours. The pylorus of each rat was ligated under ether anethesia according to the method of S. Okabe et al [Jap. J. Pharmac. 24, 357–361 (1974)]. After the pylorus ligation, aspirin (100 mg/kg) was administered orally to each rat. Seven hours after the administration, each of the animals was sacrificed under ether anesthesia to remove its stomach. After collection of the gastric juice and treatment with a 1% formalin solution, the length (mm) of each lesion formed in the glandular portion was measured. The total length (mm) of all the lesions of each rat was indicated as an ulcer index. Test medicine samples were given orally immediately after the pylorus ligation.

The results are shown in Table 3.

TABLE 3

Inhibitory Effects on Aspirin-induced Ulcer in Rats

| Samples | Dose (mg/kg, P.O.) | Ulcer index | % Inhibition |
|---|---|---|---|
| Control | — | 17.7 ± 2.3 | — |
| A | 1,000 | 0.6 ± 0.6 | 96.6 |
| L-Glutamine | 1,000 | 6.0 ± 2.2 | 66.1 |
| Aluminum sucrose sulfate | 1,000 | 3.7 ± 2.1 | 79.1 |
| Control | — | 17.5 ± 3.5 | — |
| B | 1,000 | 0.6 ± 0.6 | 96.4 |
| L-Glutamine | 1,000 | 4.5 ± 1.5 | 73.2 |
| Aluminum sucrose sulfate | 1,000 | 2.0 ± 1.1 | 88.1 |

A and B have the same meaning as defined above.

EXPERIMENT 4

Indomethacin-induced ulcer: Groups of ten male Donryu strain rats each weighing 200 to 215 g were deprived of food for 24 hours. Then, the pylorus was ligated under ether anethesia, after which indomethacin was administered subcutaneously in an amount of 25 mg/kg to each rat. Seven hours after the administration, each of the animals was scarificed under ether anethesia to remove its stomach, followed by immersion in a 1% formalin solution for ten minutes. The stomach which had been semi-fixed was incised along its greater curvature, and the length (mm) of each lesion formed in the mucous membrane was measured under a dissecting microscope (10×). The total length (mm) of all the lesions of each rat was indicated as an ulcer index. Test medicine samples were given orally ten minutes before the pylorus legation.

The results are shown in Table 4.

TABLE 4

Inhibitory Effects on Indomethacin-induced Ulcer in Rats

| Samples | Dose (mg/kg, P.O.) | Ulcer index | % Inhibition |
|---|---|---|---|
| Control | — | 16.3 ± 2.4 | — |
| A | 300 | 6.5 ± 2.2 | 60.1 |
| L-Carnosine | 300 | 17.3 ± 3.0 | ~0 |
| L-Glutamine | 300 | 9.5 ± 4.1 | 41.8 |
| Aluminum sucrose sulfate | 300 | 7.8 ± 3.0 | 52.1 |
| Control | — | 16.8 ± 2.1 | — |
| B | 300 | 6.4 ± 2.2 | 61.9 |
| L-Carnosine | 300 | 17.1 ± 3.1 | ~ 0 |
| L-Glutamine | 300 | 9.7 ± 3.9 | 42.3 |
| Aluminum sucrose sulfate | 300 | 7.4 ± 2.8 | 56.0 |

A and B have the same meaning as defined above.

EXPERIMENT 5

Histamine-induced ulcer: Groups of ten male Donryu strain rats each weighing 210 to 230 g were deprived of food for 48 hours and then administered intraperitoneally with histamine phosphate (300 mg/kg). Four hours after the administration, each of the animals was sacrificed under ether anesthesia, followed by removal of the stomach and immersion in a 1% formalin solution for ten minutes. The stomach which had been semi-fixed was incised along the greater curvature, and the length (mm) of each lesion was measured under a dissecting microscope (10×). The total length (mm) of all the lesions of each rat was indicated as an ulcer index. Test medicine samples were given orally before the histamine administration.

The results are shown in Table 5.

TABLE 5

| Inhibitory Effects on Histamine-induced Ulcer in Rats | | | |
|---|---|---|---|
| Samples | Dose (mg/kg, P.O.) | Ulcer index | % Inhibition |
| Control | — | 24.1 ± 4.7 | — |
| A | 300 | 9.6 ± 1.8 | 60.2 |
| L-Carnosine | 300 | 17.3 ± 3.2 | 28.2 |
| Aluminum sucrose sulfate | 300 | 14.4 ± 1.5 | 40.2 |
| Control | — | 23.0 ± 3.0 | — |
| B | 300 | 9.1 ± 1.9 | 60.4 |
| L-Carnosine | 300 | 18.0 ± 2.7 | 21.7 |
| N-Acetyl-L-glutamine aluminum | 2,000 | 8.5 ± 3.0 | 63.0 |
| Aluminum sucrose sulfate | 300 | 10.7 ± 2.1 | 53.5 |

A and B have the same meaning as defined above.

EXPERIMENT 6

Acute toxicity: Male and female Wister strain rats each weighing 150 to 200 g were divided into two groups, respectively, each group consisting of ten rats, and were administered orally with some of the N-acylcarnosine aluminum compounds according to the invention. The thus treated rats were visually observed for seven days after the administration.

The results are shown in Table 6.

TABLE 6

| Values of LD50 in Rats | | |
|---|---|---|
| | LD50 (mg/kg P.O.) | |
| Samples | Male | Female |
| A | >10,000 | >10,000 |
| B | >10,000 | >10,000 |

As is clearly seen from the experimental results of Tables 1 to 6, the N-acylcarnosine aluminum compounds or salts according to the invention exhibit an excellent inhibiting effect on various ulcer models. That is, when administered orally in an amount of 300 or 1,000 mg/kg to rats in the tests of Shay's ulcer, stress ulcer, aspirin-induced ulcer, indomethanocin-induced ulcer and histamine-induced ulcer, such salts are significantly effective for inhibiting any of the ulcers and hence are more excellent than any existing anti-ulcer agents.

In the acute toxicity test, even when the N-acylcarnosine aluminum salts were administered orally in an amount as large as 10 g/kg, no death of rats was recognized, and no or little change in general symptoms was observed.

Accordingly, the N-acylcarnosine aluminum salts of the present invention can be used as a digestive ulcer remedy which is higher in safety and more excellent in effectiveness than L-glutamine, N-acetyl-L-glutamine aluminum and aluminum sucrose sulfate which have now been widely used as anti-ulcer agents. The N-acyl-carnosine aluminum salts may be administered either orally or parenterally and may be used in the form of, for example, tablets, capsules, powders, granules and syrups for oral administration and also in the form of injection for parenteral administration.

The amount of administration is generally in the range of 500 to 5,000 mg/day for adults, which may be varied depending both on the age and on the symptom.

This invention will now be described in more detail with reference to certain specific Examples which are provided for purposes of illustration only and are not intended to be considered as limiting.

EXAMPLE 1

(a) A solution of 5.36 g of N-acetyl-DL-carnosine* in 100 ml of water was heated to about 40° C. To the solution was added dropwise, with vigorous stirring, 90 ml of an isopropyl alcohol solution containing 4.08 g of aluminum isopropoxide. After the addition, the reaction mixture was stirred at 40° C. for ten minutes, and any insoluble materials were removed from the mixture by filtration. The solvent was removed under reduced pressure, and to the oily residue was added isopropyl alcohol for solidification. The resulting solid was crushed and powdered. The powder was washed sufficiently with isopropyl alcohol and dried at 60° C. under reduced pressure to obtain 6.5 g (quantitative yield) of colorless powder [mp: 210° C. (decomp.)]. 5 g of the thus obtained powder was dissolved in 30 ml of water. 4.8 g of an N-acetyl-DL-carnosine aluminum salt was obtained from the solution by spray drying at 80° C.

*N-acetyl-DL-carnosine: A. Lukton and A. Sist: [J.O.C. 26, 617 (1961)] mp: 215° C. (decomp.);

IR$\nu_{max}^{KBr}$ cm$^{-1}$: 3400 (OH), 1630 (C=O), 1450, 1380.

NMR (D$_2$O)δ: 1.88 (3H, s, —COCH$_3$); 2.43 (2H, m, —CH$_2$CH$_2$NHCOCH$_3$);

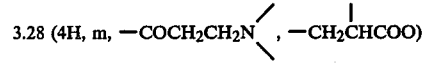

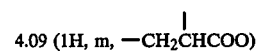

7.05, 8.10 (1H×2, s×2, imidazole ring protons).

Elementary analysis as (C$_{11}$H$_{15}$N$_4$O$_4$)Al(OH)$_2$: Calculated (%): C: 40.25, H: 5.22, N: 17.07, Al: 8.22; Found (%): C: 40.10, H: 5.41, N: 16.77, Al: 8.01.

These analytical data confirm the following structure (A).

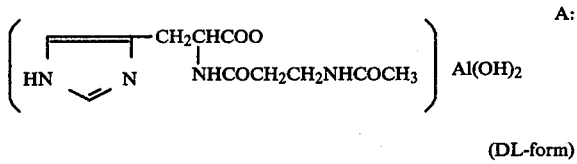

(DL-form)

(b) A solution of 4.5 g of N-acetyl-DL-carnosine in 30 ml of water was heated to about 60° C. To the solution was added dropwise, with vigorous stirring, 25 ml of an isopropyl alcohol solution containing 3.75 g of aluminum isopropoxide. After the addition, the reaction mixture was stirred at 60° C. for four hours, isopropyl alcohol was removed from the reaction mixture under reduced pressure, and any insoluble materials were removed from the residual aqueous solution by filtration. 5.1 g (quantitative yield) of an N-acetyl-DL-carnosine aluminum salt was obtained as colorless powder from the filtrate by spray drying at 80° C.

The analytical data were in strict accord with those obtained in item (a) above.

EXAMPLE 2

(a) A solution of 600 g of N-acetyl-L-carnosine dissolved in 5.2 l of water was heated to about 60° C. To the solution was added dropwise, with vigorous stirring, 3.8 l of an isopropyl alcohol solution containing 500 g of aluminum isopropoxide. After the addition, the mixture was stirred for three hours at 60° C., and then isopropyl alcohol was removed from the reaction mixture under reduced pressure. Any insoluble materials were removed from the reaction mixture by filtration. 690 g of an N-acetyl-L-carnosine aluminum salt was obtained as colorless powder from the filtrate by spray drying at 80° C.

mp: 235° C. (decomp.).
$[\alpha]_D^{20}$: +15.9° C. (C=5% in $H_2O$).
$IR\nu_{max}^{KBr}$ cm$^{-1}$: 3400 (OH), 1360 (CO), 1450, 1380.
NMR ($D_2O$)δ: 1.98 (3H, s, —COC$\underline{H}_3$); 2.53 (2H, m, —C$\underline{H}_2$C$\underline{H}_2$NHCOCH$_3$);

3.40 (4H, m, —COCH$_2$CH$_2$N, —CH$_2$CHCOO)

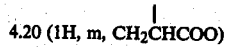

4.20 (1H, m, CH$_2$CHCOO)

7.25, 8.53 (1H×2, s×2, imidazole ring protons).

Elemental analysis as ($C_{11}H_{15}N_4O_4$)Al(OH)$_2$: Calculated (%): C: 40.25, H: 5.22, N: 17.07, Al: 8.22; Found (%): C: 40.13, H: 5.19, N: 17.01, Al: 8.27.

These analytical data confirm the following structure (B).

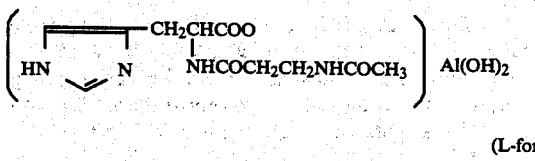

(b) A solution of 120 g of N-acetyl-L-carnosine dissolved in 1 l of water was heated to about 60° C. To the solution was added dropwise, with vigorous stirring, 800 ml of an isopropyl alcohol solution containing 100 g of aluminum isopropoxide. After the addition, the mixture was stirred for three hours at 60° C., and then isopropyl alcohol was removed from the reaction mixture under reduced pressure. Any insoluble materials were removed from the residual aqueous solution by filtration, and the filtrate was concentrated to 300 ml. The resulting solution was freeze dried to obtain 151 g of an N-acetyl-L-carnosine aluminum salt as colorless powder.

The analytical data were in strict accord with those obtained in item (a) above.

(c) A solution of 3 g of N-acetyl-L-carnosine dissolved in 25 ml of water was heated to about 60° C. To the solution was added dropwise, with vigorous stirring, 20 ml of an isopropyl alcohol solution containing 2.5 g of aluminum isopropoxide. After the addition, the mixture was stirred for three hours at 60° C. Any insoluble materials were removed from the residual aqueous solution by filtration, and the filtrate was concentrated to dryness, thereby yielding 3.5 g of an N-acetyl-L-carnosine aluminum salt as colorless powder.

The analytical data were in strict accord with those obtained in item (a) above.

EXAMPLE 3

To a solution of 0.70 g of aluminum isopropoxide dissolved in 20 ml of isopropyl alcohol was added 2.76 g of N-acetyl-L-carnosine at 60° C., and the mixture was stirred for one hour. 10 ml of water was added to the reaction mixture which was stirred for 30 minutes until it became homogeneous. After filtration of the reaction mixture, isopropyl alcohol of the filtrate was removed by evaporation under reduced pressure, and the residual aqueous solution was freeze dried to obtain 2.8 g (quantitative yield) of an N-acetyl-L-carnosine aluminum salt as colorless powder.

mp: 220° C. (decomp.).
$[\alpha]_D^{25}$: +22.8° C. (C=5% in $H_2O$).
$IR\nu_{max}^{KBr}$ cm$^{-1}$: 3400 (OH), 1630 (CO), 1390, 1300.
NMR($D_2O$)δ: 1.63 (3H, s, —COCH$_3$);

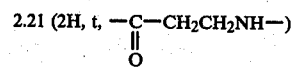

2.21 (2H, t, —C—CH$_2$CH$_2$NH—)
              ‖
              O

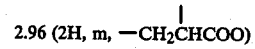

2.96 (2H, m, —CH$_2$CHCOO)

3.16 (—COCH$_2$C$\underline{H}_2$NH—);

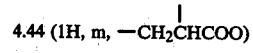

4.44 (1H, m, —CH$_2$CHCOO)

7.41, 8.81 (1H×2, s×2, imidazole ring protons).

Elemental analysis as ($C_{11}H_{14}N_4O_4$)$_3$Al: Calculated (%): C: 47.82, H: 5.48, N: 20.28; Found (%): C: 47.58, H: 5.24, N: 20.08.

These analytical data confirm the following structure (C).

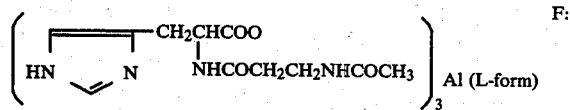

EXAMPLE 4

To a solution of 1.04 g of aluminum isopropoxide dissolved in 20 ml of isopropyl alcohol was added 2.73 g of N-acetyl-L-carnosine at 60° C. 2.9 g (quantitative yield) of an N-acetyl-L-carnosine aluminum salt was obtained as colorless powder in the same way as in Example 3.

mp: 218° C. (decomp.).
$[\alpha]_D^{25}$: +19.6° C. (C=5% in $H_2O$).
$IR\nu_{max}^{KBr}$ cm$^{-1}$: 3400 (OH), 1630 (CO), 1390, 1300.
NMR($D_2O$)δ: 1.91 (3H, s, —COCH$_3$); 2.42 (2H, t, —COC$\underline{H}_2$CH$_2$N<);

3.10 (2H, m, —CH₂C̲H̲COO)

|
3.32 (2H, t, —COCH₂C̲H̲₂NH—)

|
4.44 (1H, m, —CH₂C̲H̲COO)

7.09, 8.32 (1H×2, s×2, imidazole ring protons).

Elemental analysis as (C₁₁H₁₅N₄O₄)₂AlOH: Calculated (%): C: 45.67, H: 5.41, N: 19.37; Found (%): C: 45.84, H: 5.12, N: 19.45.

These analytical data confirm the following structure (D).

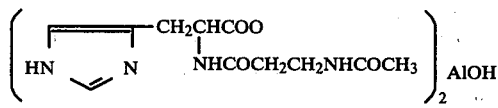

(L-form)

EXAMPLE 5

(a) N-Propionyl-L-carnosine: To a solution of 2.42 of L-carnosine dissolved in 13 ml of water was added 6.5 ml of acetone. Thereafter, 4.14 g of propionyl chloride and 7.6 g of triethylamine were simultaneously added dropwise to the solution at such a rate that the reaction mixture did not exceed 20° C. in temperature and was maintained at a pH of 7.0 to 7.5. The dropwise addition took about one hour. After the addition, acetone was evaporated under reduced pressure, and the residue was adsorbed on a strong anion exchange resin (SA-10A) in an amount of 130 ml. The anion resin was washed with water and eluted with 1 N acetic acid, and the eluant was further adsorbed on a strong cation exchange resin (SK-1B) in an amount of 10 ml. After the cation resin was washed with water and eluted with 2% aqueous ammonia, the eluant was evaporated under reduced pressure to remove the greater part of ammonia. The residue was passed through 30 ml of a weak cation exchange resin (IRC-50), and the portion of the residue which had not been adsorbed was distilled to dryness under reduced pressure to obtain a crude product. Recrystallization of the crude product from methanol-acetone (2:3) gave 1.46 g of N-propionyl-L-carnosine as colorless crystal (yield: 48%).

mp: 206°~209° C. (decomp.).
$[\alpha]_D^{25}$: +20.4° C. (C=3% in H₂O).
$IR\nu_{max}^{KBr}$ cm⁻¹: 3300 (OH), 1630 (CO), 1540, 1390.
NMR(D₂O)δ: 1.06 (3H, t, J=8 Hz, —CH₂C̲H̲₃); 2.18 (2H, q, J=8 Hz, —C̲H̲₂CH₃); 2.44 (2H, t, J=7 Hz, —NHCOC̲H̲₂CH₂NH—);

|
3.14 (2H, m, —CH₂C̲H̲COO)

3.36 (2H, t, J=7, —NHCOCH₂C̲H̲₂NH—);

|
4.44 (1H, m, —CH₂C̲H̲COO)

7.08, 8.48 (1H×2, s×2, imidazole ring protons).

Elemental analysis as C₁₂H₁₈N₄O₄: Calculated (%): C: 51.04, H: 6.44, N: 19.85; Found (%): C: 50.95, H: 6.43, N: 19.77.

(b) To a solution of 0.8 g of aluminum isopropoxide dissolved in 11 ml of isopropyl alcohol was added 1.11 g of N-propionyl-L-carnosine at 60° C., 1.3 g (quantitative yield) of an N-propionyl-L-carnosine aluminum salt was obtained in the same way as in Example 3.

mp: 228° C. (decomp.).
$[\alpha]_D^{25}$: +11.4° C. (C=3% in H₂O).
$IR\nu_{max}^{KBr}$cm⁻¹: 3400 (OH), 1640 (C=O), 1540, 1400.
NMR(D₂O)δ: 1.02 (3H, t, —COCH₂C̲H̲₃); 2.11 (2H, q, —COC̲H̲₂CH₃); 2.40 (2H, t, —COC̲H̲₂CH₂NH—);

|
3.08 (2H, m, —CH₂C̲H̲COO)

3.28 (2H, t, —COCH₂C̲H̲₂NH—);

|
4.44 (1H, m, —CH₂C̲H̲COO)

7.08, 8.26 (1H×2, s×2, imidazole ring protons).

Elemental analysis as (C₁₂H₁₇N₄O₄)Al(OH)₂: Calculated (%): C: 42.10, H: 5.61, N: 16.37; Found (%): C: 41.88, H: 5.83, N: 16.12.

These anlytical data confirm the following structure (E).

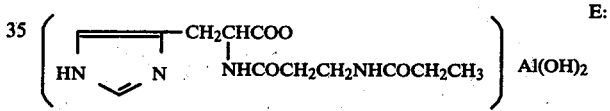

(L-form)

EXAMPLE 6

To a solution of a 0.72 g of aluminum isopropoxide dissolved in 15 ml of isopropyl alcohol was added 1.97 g of N-propionyl-L-carnosine at 60° C. Thereafter, 2.1 g (quantitative yield) on an N-propionyl-L-carnosine aluminum salt was obtained as colorless power in the same way as in Example 3.

mp: 220° C. (decomp.).
$[\alpha]_D^{25}$: +14.5° C. (C=1% in H₂).
$IR\nu_{max}^{KBr}$ cm⁻¹: 3400 (OH), 1640 (CO), 1540.
NMR(D₂O)δ: 1.02 (3H, t, —CH₂C̲H̲₃); 2.10 (2H, q, —C̲H̲₂CH₃); 2.42 (2H, t, —COC̲H̲₂CH₂NH—);

|
3.15 (2H, m, —CH₂C̲H̲COO)

3.35 (2H, t, —COCH₂C̲H̲₂NH—)

|
4.44 (1H, m, —CH₂C̲H̲COO)

7.80, 8.27 (1H×2, s×2, imidazole ring protons).

Elemental analysis as (C₁₂H₁₇N₄O₄)₂AlOH: Calculated (%): C: 47.51, H: 5.83, N: 18.48; Found (%): C: 47.37, H: 5.78, N: 18.37.

These analytical data confirm the following structure (F).

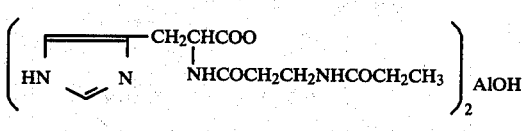

(L-form)

EXAMPLE 7

(a) N-Heptanoyl-L-carnosine: To a solution of 2.42 g of L-carnosine dissolved in 13 ml of water was added 6.5 ml of acetone. 6.36 g of heptanoyl chloride was then added to the solution which was treated in the same procedure as described in item (a) of Example 5 to obtain a crude product. Recrystallization of the crude product from water-acetone (1:2) gave 1.66 g of N-heptanoyl-L-carnosine as colorless crystal (yield: 46%).

mp: 214°~217° C. (decomp.).
$[\alpha]_D^{25}$: +4.7° C. (C=2% in $H_2O$).
$IR\nu_{max}^{KBr}$ cm$^{-1}$: 3290, 1635, 1530, 1400.
NMR($D_2O$)δ: 0.72 (3H, m, —$CH_3$); 0.86~1.56 (8H, m, —$CH_2$×4); 2.06 (2H, t, J=7 Hz, —$COCH_2CH_2$—); 2.35 (2H, t, J=7 Hz, —$NHCOCH_2CH_2NH$);

2.94 ~ 3.14 (2H, m, —$CH_2\overset{|}{C}HCOO$)

3.26 (2H, t, J=7 Hz, —$NHCOCH_2C\underline{H}_2NH$);

4.26 ~ 4.44 (1H, m, —$CH_2\overset{|}{C}HCOO$)

7.10, 8.42 (1H×2, s×2, imidazole ring protons).

Elemental analysis as $C_{16}H_{26}N_4O_4$: Calculated (%): C: 56.77, H: 7.76, N: 16.56; Found (%): C: 56.81, H: 7.85, N: 16.38.

(b) To a solution of 0.68 g of aluminum isopropoxide dissolved in 15 ml of isopropyl alcohol was added 1.13 g of N-heptanoyl-L-carnosine at 60° C. 1.3 g (quantitative yield) of an N-heptanoyl-L-carnosine aluminum salt was obtained as colorless powder in the same way as in Example 3.

mp: 280° C.<(decomp.).
$[\alpha]_D^{25}$: +0.4° C. (C=1% in $H_2O$).
$IR\nu_{max}^{KBr}$ cm$^{-1}$: 3400 (OH), 2930, 2860 (Alkyl), 1640 (CO), 1540.
NMR($D_2O$)δ: 0.80 (3H, t, —$CH_2C\underline{H}_3$); 1.20 (8H, m, —$CH_2$—×4); 2.12 (2H, t, —$CH_2C\underline{H}_2CO$—); 2.40 (2H, t, —$COC\underline{H}_2CH_2NH$—);

3.07 (2H, m, —$CH_2\overset{|}{C}HCOO$)

3.31 (2H, t, —$COCH_2C\underline{H}_2NH$—);

4.44 (1H, m, —$CH_2\overset{|}{C}HCOO$)

7.06, 8.28 (1H×2, s×2, imidazole ring protons)

Elemental analysis as ($C_{16}H_{25}N_4O_4$)Al(OH)$_2$: Calculated (%): C: 48.23; H: 6.84, N: 14.06; Found (%): C: 48.03, H: 6.87, N: 13.77.

These analytical data confirm the following structure (G).

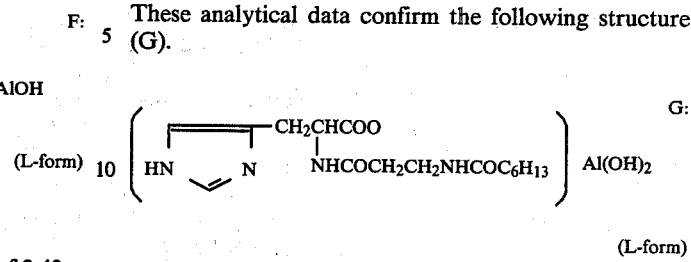

(L-form)

EXAMPLE 8

(a) N-Benzoyl-L-carnosine: To a solution of 2.42 g of L-carnosine dissolved in 13 ml of water was added 6.5 ml of acetone. Thereafter, 6.32 g of benzoyl chloride was added to the solution which was treated in the same procedure as described in item (a) of Example 5 to obtain a crude product. Recrystallization of the crude product from methanol-acetone (2:3) gave 1.69 g of N-benzoyl-L-carnosine as colorless crystal (yield: 48%).

mp: 217°~219° C. (decomp.).
$[\alpha]_D^{25}$: +10.3° C. (C=1% in $H_2O$).
$IR\nu_{max}^{KBr}$ cm$^{-1}$: 3280, 1640, 1520, 1385.
NMR($D_2O$)δ: 2.48 (2H, t, J=7 Hz, —$COC\underline{H}_2CH_2NH$—);

3.02 (2H, m, —$CH_2\overset{|}{C}HCOO$)

3.46 (2H, t, J=7 Hz, —$COCH_2C\underline{H}_2NH$—);

4.37 (1H, m, —$CH_2\overset{|}{C}HCOO$)

6.99 [1H, s, imidazole ring proton (5-position)]; 7.1~7.6 (5H, m, benzene ring protons); 8.14 [1H, s, imidazole ring proton (2-position)].

Elemental analysis as $C_{16}H_{18}N_4O_4$: Calculated (%): C: 58.16, H: 5.50, N: 16.96; Found (%): C: 58.21, H: 5.65, N: 16.93.

(b) To a solution of 0.8 g aluminum isopropoxide dissolved in 15 ml of isopropyl alcohol was added 1.27 g of N-benzoyl-L-carnosine at 60° C. 1.5 g (quantitative yield) of an N-benzoyl-L-carnosine aluminum salt was obtained as colorless powder in the same way as in Example 3.

mp: 280° C.<(decomp.).
$[\alpha]_D^{25}$: +6.2° C. (C=1% in $H_2$).
$IR\nu_{max}^{KBr}$ cm$^{-1}$: 3400 (OH), 1630 (CO), 1540, 1400.
NMR($D_2O$)δ: 2.55 (2H, t, —$COC\underline{H}_2CH_2NH$—);

3.07 (2H, m, —$CH_2\overset{|}{C}HCOO$)

3.55 (2H, t, —$COCH_2C\underline{H}_2NH$—)

4.44 (1H, m, —$CH_2\overset{|}{C}HCOO$)

6.99 [1H, s, imidazole ring proton (5-position)]; 7.44 (5H, m, benzene ring protons); 8.08 [1H, s, imidazole ring proton (2-position)].

Elemental analysis as $(C_{16}H_{17}N_4O_4)Al(OH)_2$: Calculated (%): C: 49.23, H: 4.92, N: 14.36; Found (%): C: 49.18, H: 4.86, N: 14.18.

These analytical data confirm the following structure (H).

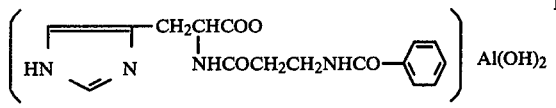

(L-form)

EXAMPLE 9

(a) N-(o-Methoxy)benzoyl-L-carnosine: To a solution of 2.42 g of L-carnosine dissolved in 13 ml of water was added 6.5 ml of acetone. Thereafter, 7.67 g of o-methoxy benzoyl chloride was added to the solution which was treated in the same procedure as described in item (a) of Example 5 to obtain a crude product. The crude product was very hygroscopic and then washed with ether to give 1.54 g of N-(o-methoxy)benzoyl-L-carnosine as colorless crystal (yield: 40%).

mp: 203° C. (decomp.).

$[\alpha]_D^{25}$: +7.6° C. (C=1% in $H_2O$).

$IR\nu_{max}^{KBr}$ cm$^{-1}$: 3380, 1630.

NMR(CD$_3$OD)$\delta$: 2.56 (2H, t, J=7 Hz, —COC$\underline{H}_2$CH$_2$NH—);

3.16 (2H, m, —CH$_2$C$\underline{H}$COO)

3.60 (2H, t, J=7 Hz, —COCH$_2$C$\underline{H}_2$NH—); 3.86 (3H, s, —OC$\underline{H}_3$)

4.55 (1H, m, —CH$_2$C$\underline{H}$COO)

6.85~7.85 (5H, m, benzene ring prontons and imidazole ring proton); 8.33 (1H, s, imidazole ring proton).

Elemental analysis as $C_{17}H_{20}N_4O_5$: Calculated (%): C: 56.65, H: 5.60, N: 15.55; Found (%): C: 56.61, H: 5.58, N: 15.61.

(b) To a solution of 0.68 g of aluminum isopropoxide dissolved in 15 ml of isopropyl alcohol was added 1.20 g of N-(o-methoxy)benzoyl-L-carnosine at 60° C. 1.40 g (quantitative yield) of an N-(o-methoxy)benzoyl-L-carnosine aluminum salt was obtained as colorless powder in the same way as in Example 3.

mp: 280° C.<(decomp.).

$[\alpha]_D^{25}$: +2.7° C. (C=1% in $H_2O$).

$IR\nu_{max}^{KBr}$ cm$^{-1}$: 3400 (OH), 1630 (CO), 1540, 1400, 1310.

NMR(D$_2$O)$\delta$: 2.56 (2H, t, —COC$\underline{H}_2$CH$_2$NH—)

3.29 (2H, m, —CH$_2$C$\underline{H}$COO)

3.55 (2H, t, —COCH$_2$C$\underline{H}_2$NH—); 3.83 (3H, s, —OCH$_3$);

4.44 (1H, m, —CH$_2$C$\underline{H}$COO)

6.95~7.65 (5H, m, benzene ring protons and imidazole ring proton); 7.96 (1H, s, imidazole ring proton).

Elemental analysis as $(C_{17}H_{19}N_4O_5)Al(OH)_2$: Calculated (%): C: 48.57, H: 5.05, N: 13.33; Found (%): C: 48.42, H: 4.92, N: 13.18.

These analytical data confirm the following structure (I).

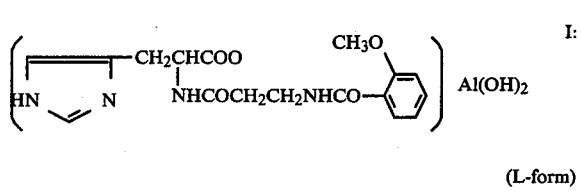

(L-form)

EXAMPLE 10

Preparation: 1 g of a digestive ulcer remedy prepared in the form of granules contains the following ingredients.

| Ingredients | Quantity/g |
|---|---|
| Compound B | 200 mg |
| Milk sugar | 400 mg |
| Corn starch | 400 mg |
| Total: | 1,000 mg |

Compound B is the same as defined above.

What is claimed as new and is intended to be secured by Letters Patent is:

1. An N-acylcarnosine aluminum salt of the formula (I),

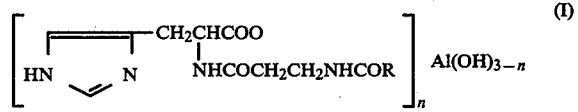

where in R represents a lower alkyl group having 1 to 6 carbon atoms, a phenyl group or a lower alkoxy group-substituted phenyl group, and n represents an integer of 1 to 3.

2. The N-acylcarnosine aluminum salt according to claim 1, wherein n is equal to 1.

3. The N-acylcarnosine aluminum salt according to claim 1, wherein n is equal to 2.

4. The N-acylcarnosine aluminum salt according to claim 1, wherein n is equal to 3.

5. The N-acylcarnosine aluminum salt according to claim 1, wherein R is a lower alkyl group having 1 to 6 carbon atoms.

6. The N-acylcarnosine aluminum salt according to claim 1, wherein R is an acetyl group.

7. A process for preparing an N-acylcarnosine aluminum salt of the formula (I),

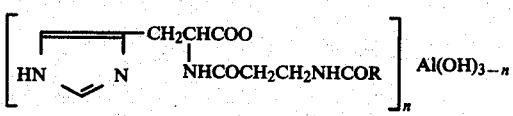 (I)

wherein R represents a lower alkyl group having 1 to 6 carbon atoms, a phenyl group or a lower alkoxy group-substituted phenyl group, and n represents an integer of 1 to 3, which comprises reacting an N-acylcarnosine of the formula (II),

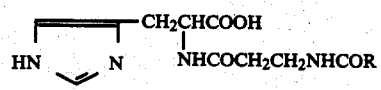 (II)

wherein R has the same meaning as defined above, with an aluminum alkoxide in the presence of a solvent, and removing said solvent and side produced alcohols from the reaction solution.

8. The process according to claim 7, wherein said aluminum alkoxide is selected from the group consisting of aluminum methoxide, aluminum ethoxide, aluminum isopropoxide, aluminum t-butoxide and aluminum cyclohexyloxide.

9. The process according to claim 7, wherein said solvent is selected from the group consisting of water, methanol, ethanol, isopropanol, butanol and a mixture thereof.

10. The process according to claim 7, wherein the reaction is conducted at temperatures ranging from room temperature to 80° C.

11. A process for preparing an N-acylcarnosine aluminum salt of the formula (I),

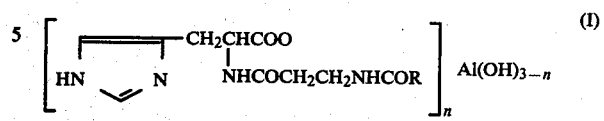 (I)

wherein R represents a lower alkyl group having 1 to 6 carbon atoms, a phenyl group or a lower alkoxy group-substituted phenyl group, and n represents an integer of 1 to 3, which comprises reacting an N-acylcarnosine of the formula (II),

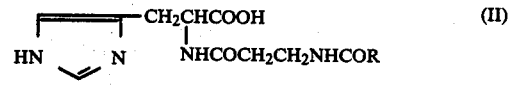 (II)

wherein R has the same meaning as defined above, with an inorganic aluminum salt, and subjecting the reaction mixture to separation by ion exchange.

12. The process according to claim 11, wherein said inorganic aluminum salt is selected from the group consisting of an aluminum sulfuric acid salt, an aluminum nitric acid salt and an aluminum chloric acid salt.

13. The process according to claim 11, wherein said ion exchange separation is conducted with the use of a weakly basic anion exchange resin.

14. The process according to claim 11, wherein said anion exchange resin is used twice or three times equivalent of the N-acylcarnosine.

15. A remedy for inhibiting a digestive ulcer, which comprises an effective amount of the N-acylcarnosine aluminum salt of claim 1 in a suitable carrier.

* * * * *